(12) United States Patent
Daggy et al.

(10) Patent No.: US 6,372,253 B1
(45) Date of Patent: Apr. 16, 2002

(54) RAPIDLY DISINTEGRATING METHYLCELLULOSE TABLETS

(75) Inventors: Bruce Daggy, Pine Brook; Naresh I Mehta, Ledgewood; Priyashri Nayak, Randolph, all of NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/485,625

(22) PCT Filed: Aug. 21, 1998

(86) PCT No.: PCT/US98/17440

§ 371 Date: Feb. 14, 2000

§ 102(e) Date: Feb. 14, 2000

(87) PCT Pub. No.: WO99/09959

PCT Pub. Date: Mar. 4, 1999

Related U.S. Application Data

(60) Provisional application No. 60/081,644, filed on Apr. 14, 1998, and provisional application No. 60/056,899, filed on Aug. 22, 1997.

(51) Int. Cl.[7] .................................................. A61K 9/20

(52) U.S. Cl. .................... 424/465; 424/464; 514/772.3; 514/778; 514/781; 514/784

(58) Field of Search ................................. 424/464, 465, 424/470

(56) References Cited

U.S. PATENT DOCUMENTS

| 4,017,598 A | | 4/1977 | Ohno et al. ..................... 424/35 |
| 5,759,580 A | * | 6/1998 | Jans et al. ................... 424/489 |
| 5,879,706 A | * | 3/1999 | Carter et al. ................. 424/464 |

FOREIGN PATENT DOCUMENTS

| DE | 2518270 A | * | 3/1976 | ............ A61K/3/10 |

* cited by examiner

*Primary Examiner*—James M. Spear
(74) *Attorney, Agent, or Firm*—Dara L. Dinner; Stephen Venetianer; Charles M. Kinzig

(57) ABSTRACT

The present invention relates to a novel pharmaceutical composition and process for preparing swallowable methylcellulose tablets that disintegrate rapidly and meet USP disintegration standards in 0.1N hydrochloric acid as well as water.

10 Claims, No Drawings

RAPIDLY DISINTEGRATING METHYLCELLULOSE TABLETS

This application is a 371 of PCT/US98/17440 filed Aug. 21, 1998 which claims benefit of No. 60/056,899 filed Aug. 22, 1997 which claims benefit of No. 60/081,644 filed Apr. 14, 1998.

FIELD OF THE INVENTION

The present invention relates to an improved process for preparing compressed methylcellulose containing tablets which meet USP disintegration standards.

BACKGROUND OF THE INVENTION

The history of cellulose ethers, such as methylcellulose and carboxymethyl-cellulose, supports that these agents have effectiveness as bulk laxatives. Their mechanism of action involves increasing both the water content of, and the bulk content of the stool, as well as lubricating the stool; thereby relieving constipation.

Cellulose ethers have been administered as bulk laxatives in dosage forms comprising of tablets, suspensions, and bulk powders; the latter as sugar-free or in compositions containing high amounts of sugar.

Cellulose ethers administered as suspensions in water may contain high concentrations of sucrose or other sugars and flavors. In such formulations, the sugar competes with the cellulose ether for available water, thereby preventing the cellulose ether from hydrating sufficiently to form a gel. The advantages of using a suspension formulation is that the cellulose either is dispersed sufficiently to avoid any significant lumping in the digestive tract. However, the suspensions are viscous, semi-gelatinous, and visually unappealing to the consumer. Another disadvantage is the unpalatability of the suspensions due to the slimy mouth feel and extreme sweetness of such suspensions. Hence, these dosage forms have not gained significant customer acceptance.

Bulk powders of cellulose ethers often exhibit lumping of individual particles and gelatin and thus, remain undissolved as they pass through the digestive tract. That the products are undissolved means that this will prevent hydration and gelling of the powder and does not provide efficacy. Additionally, administration of bulk powders has caused cramping, nausea, and vomiting in some patients. Therefore, bulk powders are not the preferred dosage form for cellulose ethers.

Palatable and visually appealing bulk powders have, however, been accomplished by addition of water or another aqueous liquid to a dry powder mix of a water-soluble cellulose ether and a dispersing agent/sweetening component, typically sugar. This technology is disclosed in South African patent No. 84,1044, published Sep. 26, 1984. The pitfall with these compositions is that they contain about 400 calories of nutritive value per dose, primarily due to the high sugar content. This high caloric value is not acceptable to the average consumers or to users suffering from blood sugar disorders, including diabetics. Elderly people are normally, the common strata of the population that suffers from constipation and the more frequent users of laxatives, and are also commonly suffering with blood sugar disorders. The consumption of large quantities of sugar could aggravate blood sugar disorders.

Sugar encrusted cellulose ethers have been proposed as alternatives to the bulk powders containing high amounts of sugar. Such formulations have 1) less sugar such as natural sugar or combination of sugars such as sucrose, glucose, fructose or corn syrup solids; 2) lower caloric value; and 3) are readily dispersed in cold aqueous liquids.

Citrucel® Orange Flavor, a bulk forming laxative containing methylcellulose as its active ingredient, was first introduced into the market in 1986. This product contains 15 g of sucrose in a 19 g adult dose, which corresponds to a 2 g dose of methylcellulose. To decrease the sugar content of this product, a natural flavored formula lower in caloric value, and containing only 1 g sucrose, was developed and introduced in 1988. Additional patent protection for this product has focused on producing a sugar-free and virtually calorie-free powder. The product has a sugar-free sweetener, a dispersing agent, other excipients, and flavoring and was marketed in 1991 as Sugar Free Citrucel® Orange Flavor.

There still remains a need in the art to develop a rapidly disintegrating solid dosage form of a bulk agent, preferably methylcellulose, which is convenient to take and transport, sugar free, and easily administered to the consumer having blood sugar disorders or diabetics, for instance.

SUMMARY OF THE INVENTION

The present invention relates to an improved process for preparing methylcellulose tablets which are readily dispersible and meet United States Pharmacopoeia standards for disintegration. The methylcellulose is compressed into tablets which contain a suitable diluent, in preferred w/w ratios. Preferably the tablets rapidly disintegrate, in-vitro in 0.1N hydrochloric acid and water at $37 \pm 0.5°$ C.

DETAILED DESCRIPTION OF THE INVENTION

There is a common belief that tableted cellulose ethers do not readily dissolve in the digestive tract because these cellulose ethers are highly hygroscopic. The outer portion of the tablet is said to form a gel-like hydrate that prevents the tablet from breaking up and greatly retards the hydration of the inner portion of the tablet. The present invention overcomes this art recognized problem and involves preparation of a novel composition, and process of making, by which a rapidly disintegrating tablet of methylcellulose is prepared. Preferably, all excipients employed to prepare the tablets of this invention are sugar-free.

The tablets are prepared by a novel process involving a high-shear wet granulation method, followed by fluidized bed drying, milling, mixing with the other ingredients, and compression.

The present invention is to a methylcellulose tablet which comprises methylcellulose, at least one diluent or filler, and other suitable excipients well known to those skilled in the art. In some instances it is recognized that the diluent/filler and the disintegrating agent may be the same.

The tablet formulations of the present invention are advantageous over other dosage forms of methylcellulose because of their convenience of administration and rapid disintegration. This is in contrast to tablets of methylcellulose, formulated as 100% w/w methylcellulose in a 0.5 gm caplet which have been found not to disintegrate in 0.1N HCl solution, using a conventional disintegration apparatus even after two hours. The present tablets should disintegrate in 0.1N HCl from about 20 to about 30 minutes, preferably from about 10 to about 19 minutes, and more preferably less than 10 minutes; and in water, the tablets should disintegrate from about 25 to about 30 minutes, preferably from about 15 to about 24 minutes, and more preferably less than 15 minutes.

It has been found that low molecular weight (mw) methylcellulose is less effective for use as a laxative, and therefore is less desirable for use in a rapidly disintegrating tablet formation. Higher molecular weight methylcellulose is therefore both desirable and necessary in the present invention. The fibers must have a sufficient viscosity to gel and retain water in the gut to provide the stool bulking and softening for laxation use.

By using the testing methods for methylcellulose under standard conditions, such as those found in the USP XXII, p. 894, Apparent Viscosity method for Methylcellulose, or as discussed in Handbook of Pharmaceutical Excipients, APhA, a preferred methylcellulose for use herein should have a viscosity of >1000 centipoises (cps), preferably >2000 centipoises, more preferably >3000 centipoises, and most preferably >4000 centipoise. Higher molecular weight methylcellulose than those described is also desirable, however, the commerical availability of this grade of methylcellulose being the limiting feature. At present the upper limit of commercially available methylcellulose is about 6000 cps, which is encompassed within the scope of this invention. One presently available methylcellulose product for use herein is Methocel A4M, made by Dow Chemical Company, Midland Mich. as Dow Methocel A4M, having a viscosity of about 3000 to about 5,600 cps, which is within 75 to 140% of the desired target viscosity herein.

Preferred swellable diluents or fillers for use in this formulation include, but are not limited to, various grades of microcrystalline cellulose, such as Avicel PH101, Avicel PH102, & Avicel PH200; Corn starch; or Starch 1500.

Preferably the diluent is microcrystalline cellulose. A preferred size of microcrystalline cellulose is from about 50 to 180 micron, more preferably about 50. Avicel PH101 has a mean particle size of about 50; Avicel PH 102 has a mean particle size of about 100; and Avicel PH 200 has a mean particle size of about 190 microns. Preferably the preferred microcrystalline cellulose is Avicel PH 101.

It is noted that the ratio of methylcellulose to diluent will depend upon the diluent chosen, and is within the skill of the art to determine with preciseness the necessary ratios.

Suitable ratios for particular diluents are described below, however, to provide greater assistance (in % w/w) ratios:

For Methylcellulose: microcrystalline cellulose, from about 2:1 to about 14:1. Preferably for Avicel PH 101 from about 2.2–13.5:1; for Avicel PH 102 from about 2.4–8.3:1; and for Avicel PH 200 from about 2.4–4:1.

For Methylcellulose:Corn starch from about 7.5 to about 15, preferably from about 13.5:1; and For Methylcellulose:Starch 1500, from about 2.0 to about 5.0:1, preferably from about 2.4:1.

In addition to the above noted diluents or fillers, additional components include but are not limited to, a wetting agent, a (super)disintegrant, a binding agent, dye(s) or colouring agents, and lubricants, are preferably used to prepare a tablet that is wetted readily, and is rapidly disintegrated in 0.1N hydrochloric acid and water, the USP test standard test for methylcellulose.

A preferred wetting agent is sodium lauryl sulfate.

A preferred lubricant is magnesium stearate.

A preferred binder is polyvinylpyrrolidone, or PVP, such as Povidone 29K/32.

A preferred disintegrating agent is sodium starch glycolate, such as Explotab®.

As various excipients and diluents will be formulated together, and used in combinations herein, suggested % w/w ratios for various formulations are presented below:

Methylcellulose:sodium lauryl sulfate (SLS), from about 60 to about 170:1, preferably from about 155:1–170:1;

Methylcellulose:Povidone, preferably PVP 29K/32, from about 8 to about 22:1, preferably from about 10.4:1–16.7:1;

Methylcellulose:Magnesium stearate from about 50 to about 150;1, preferably from about 58–132:1;

Sodium lauryl sulfate:Explotab:Avicel PH 101®: Povidone 29K/32:Magnesium stearate include: 0.35–0.46:3.05–6.17:4.38–27.13:4.38–6.66:0.76–1.14

Sodium lauryl sulfate:Explotabl:Avicel PH 102®: Povidone 29K/32:Magnesium stearate include: 0.35–0.46:4.9–6.17:9.21–25.53:4.38–6.66:0.76–1.14

Sodium lauryl sulfate:Avicel PH 200®: Povidone 29K/32:Magnesium stearate include: 0.38–0.42:19.27–25.53:5.99–6.66:0.94–1.04

Sodium lauryl sulfate:Explotab®:Corn starch: Povidone 29K/32:Magnesium stearate include: 0.36–0.38:3.66–7.07:4.35–4.68:4.35–4.68:0.88–0.95

Sodium lauryl sulfate:Explotab®:Starch 1500®: Povidone 29K/32:Magnesium stearate include: 0.36–0.38:3.66–7.07:24.05–25.89:4.35–4.68:0.88–0.95

Not wishing to be limited to the explicit excipients noted above, the following alternative agents may be used herein.

Alternatives lubricants to magnesium stearate include, but are not limited to, calcium stearate, sodium stearate, Cab-O-Sil, Syloid, stearic acid and talc.

Alternatives to PVP include but are not limited to, hydroxypropyl cellulose, hydroxypropyl methylcellulose, acacia, gelatin, tragacanth, pregelatinized starch and starch.

Alternatives disintegrants to Explotab include but are not limited to, sodium carboxymethyl-cellulose, Ac-di-sol®, carboxymethylcellulose, veegum, alginates, agar, guar, tragacanth, locust bean, karaya, pectin, and crospovidone.

Alternative wetting agents to sodium lauryl sulfate, include but are not limited to, magnesium lauryl sulfate.

As noted above, all of these formulations can be prepared with and without sugar, a sugar-free formulation can also be administered easily to consumers with blood sugar disorders or to diabetics in need of such preparations.

The amount of methylcellulose present in each dose, as well as the number of doses of laxitive taken per day, will depend somewhat on the age, sex, size of the patient, severity of the patient's particular problem, the advice of the treating physician, if any, and the particular taste and habits of the patient. Accordingly, the tablets of this invention are advantageously administered in a single dose which may contain as much as 500 to 1000 mg of methyl cellulose tablet, or in a plurality of smaller doses containing as little as 250 mg per tablet. Most preferably, for laxative effect, each tablet will contain about 500 mg methylcellulose and the patient may take 1 to 2 tablets per dose. A dosage of 1000 mg should adequately provide optimal laxative efficacy. Therefore, a preferred range of methylcellulose per tablet is optimally from about 450 to 550 mg, preferably about 500 mg; or alternatively from about 200 to about 300 mg for a smaller tablet, preferably about 250 mg; or even in increments of about 125 mg tablet, i.e. 75 to 175 mg per tablet.

While preferably the compressed tablets are uncoated, they may, if desired, be coated with any suitable coating agent well known in the art. Suitably the coating agents are those used for immediate release purposes and will dissolve in the gastric juices. Such coating agents are well known to those skilled in the art and include, but are not limited to hydroxypropyl methylcellulose, or methyl cellulose, or 20% w/w Opadry II, orange in water.

As well readily be seen by the working examples, there are various combinations of intra and extragranular mixing which are possible using the ingredients herein. All are encompassed within the scope of this invention. Generally, the high viscosity methylcellulose, such as Methocel A4M, will first be granulated with a binder, such as povidone, a wetting agent, such as sodium lauryl sulfate, and a suitable colouring agent to form the intragranular mixture which is then granulated. These granular components are then admixed with additional wetting agents, and disintegrating agents and finally blended with lubricant. This final granular mixture is then blended and compressed into the tablets of the present invention.

Therefore, another aspect of the present invention is a process for preparing a tablet formulation which process comprises:
   a) blending together to form an intragranular mixture high viscosity methylcellulose of >3000 cps; a diluent selected from microcrystalline cellulose, corn starch, or Starch 1500, or a mixture thereof, a lubricating agent and optionally a disintegrant; and
   b) adding to the mixture of step (a), a PVP aqueous solution, or alternatively spraying the mixture of step (a) with a PVP aqueous solution; and preparing granulates; and
   c) blending together an extragranular mixture of a wetting agent; a lubricating agent; a diluent; and a disintegrant, or a mixture thereof; and
   d) compacting the granulates of step (b) with the extragranular mixture of step (c).

Preferably, in this process the extragranular components includes microcrystalline cellulose, sodium lauryl sulfate, sodium starch glycolate, and magnesium stearate. Alternatively, the extragranular components are starch, sodium lauryl sulfate, sodium starch glycolate, and magnesium stearate.

Another aspect of this invention is a process for the manufacture of a pharmaceutical tablet, which process comprises mixing
   a) granulates comprising high viscosity methylcellulose of >3000 cps; a diluent selected from microcrystalline cellulose, corn starch, Starch 1500, or mixtures thereof; and optionally together with an intra-granular disintegrant, and/or wetting agent; with
   b) an extra-granular disintegrant, and wetting agent, and optionally an extra-granular lubricant and excipient(s); and
   c) compressing into a tablet.

Another aspect of the present invention is the method of relieving constipation by increasing the water content of the stool, or by providing a lubricating effect on the stool in a mammal in need thereof, which method comprises administering to said mammal, an effective amount of a high viscosity methylcellulose compressed into a tablet with a suitable diluent.

METHODS OF PREPARATION

The following examples illustrates the invention but is not intended to limit the scope thereof. All parts and percentages are by weight unless otherwise indicated. The disintegration time of the formulation described in the Tables below were obtained by using a conventional disintegration apparatus.

EXAMPLE 1

TABLE I

| Swallowable Methylcellulose Tablets | | |
|---|---|---|
| Formula Ingredient | g/tablet | (% w/w) |
| Phase A | | |
| Methocel A4M | 0.5000 | 69.35 |
| Avicel PH101 ® | 0.0370 | 5.13 |
| Sodium lauryl sulfate | 0.0015 | 0.21 |
| Povidone 29K/32 | 0.0480 | 6.66 |
| Dye/Coloring Agent | 0.0010 | 0.14 |
| DI water | q.s. | q.s. |
| Phase B | | |
| Phase A | 0.5875 | 81.48 |
| Sodium lauryl sulfate | 0.0015 | 0.21 |
| Avicel PH200 ® | 0.1245 | 17.27 |
| Magnesium stearate | 0.0075 | 1.04 |
| TOTAL | 0.7210 | 100.00 |

The process of preparing the rapidly disintegrating tablet of methylcellulose is carried out using specified quantities of ingredients, such as those mentioned in TABLE I above, using the following steps:

1. Preparation of Povidone K29/32 (PVP) Solution

The specified amount of PVP was weighed and added to the weighed quantity of water and stirred till all the PVP was dissolved completely.

2. Preparation of Phase A

Accurately weighed amounts of Methocel A4M, sodium lauryl sulfate, Avicel PH101, and a colouring agent, such as any suitable FD&C Aluminum lake, were transferred to a Key Hi-shear granulator and mixed for about 10 minutes with impellor speed at 135 rpm and chopper speed at 10%. The PVP solution was sprayed onto the mixture in the granulator at a rate of approx. >200 mL/min. Once addition of PVP solution was complete, the chopper was stopped. The mixing was continued in the granulator till resistance reads about 130–135 watts and the time noted to reach that wattage. A sample was withdrawn from the wet granulation to record loss on drying (% LOD). The moist granules were dried in the Aeromatic Fluid bed dryer in portions till the % LOD reading approximated 1.0–3.0%. The temperature of the air in the fluid bed dryer was maintained in approx. 90–95° C. and the sample was found to be dry at an outlet air temperature of approx. 32–52° C. The dried granules were milled through a 12# screen in the Fitz Mill at a high speed. The granules were weighted and percent yield calculated. The moisture content was measured for the dry granules. A sample from the granules was withdrawn and analyzed for particle size distribution, bulk and tap density, flow index, and moisture studies. The granules were weighted and ingredients of Phase B were calculated based on weight of remaining granules.

3. Preparation of the Final Blend

To the weighed milled granules produced in Phase A above, specified amounts of sodium lauryl sulfate, and Avicel PH200 were added into the V-blender and mixed about 10 minutes. Magnesium stearate was then added to the blend and mixed for an additional 3 minutes or so. Samples from different sections of the V-blender were drawn and submitted for analyzing blend uniformity. A sample from the final blend was analyzed for particle size distribution, bulk and tap density, flow index, and moisture studies. The granules were then weighed.

4. Compression of methylcellulose tablets

The final blend was charged into the hopper of a Stokes signal punch 'F' tablet press and compressed into caplets with a suitable tooling.

Target tablet hardness desired is between 10 and 25, preferably 8–12 SCU; a preferred target weight of each tablet of less than 750 mg; an estimated friability of less than 2.0%, more preferably less than 1.0%, and target disintegration times below 30 minutes in water and acid (shorter disintegration times, less than 10 minutes, more preferably less than 8 minutes, in 0.1N HCl and less than 15 minutes in water, more preferably about 8 minutes, are preferred). The tablets were packaged in Ziplock bags. The tablets were tested for weight variation, hardness, disintegration in acid and water, friability, moisture (% LOD), thickness, viscosity, and content uniformity.

The formulation in TABLE I exhibited an average disintegration time of less than 4 minutes in 0.1N HCl and less than 7 minutes in water at 37$^{\pm 0.5°}$ C. using the automated disintegration apparatus. Using conventional disintegration apparatus the formulation of Table I yielded an average disintegration time of less than 5 minutes in acid and less than 9 minutes in water.

EXAMPLE 2

A formulation containing both Avicel PH 101® and Explotab®, intra and extragranularly as shown in TABLE II below, exhibited an average disintegration time of less than 1 minute in 0.1N HCl at 37$^{\pm 0.5°}$ C. using the automated disintegration apparatus.

TABLE II

Swallowable Methylcellulose Tablets

| Formula Ingredient | g/tablet | (% w/w) |
|---|---|---|
| Phase A | | |
| Methocel A4M | 0.5000 | 60.31 |
| Avicel PH 101 ® | 0.0370 | 4.46 |
| Sodium lauryl sulfate | 0.0015 | 0.18 |
| Povidone 29K/32 | 0.0370 | 4.46 |
| Explotab ® | 0.0300 | 3.62 |
| DI water | q.s. | q.s. |
| Phase B | | |
| Phase A | 0.6055 | 73.03 |
| Sodium lauryl sulfate | 0.0017 | 0.21 |
| Sodium starch glycolate | 0.0253 | 3.05 |
| Avicel PH 101 ® | 0.1880 | 22.67 |
| Magnesium stearate | 0.0086 | 1.04 |
| TOTAL | 0.8291 | 100.00 |

EXAMPLE 3

A formation containing Avicel PH101® intragranularly, extragranular Avicel PH 102® and Explotab®, intra and extragranularly, as shown below in TABLE III exhibited an average disintegration time of less than 3 minutes in 0.1N HCl at 37$^{\pm 0.5°}$ C. using the automated disintegration apparatus.

TABLE III

Swallowable Methylcellulose Tablets

| Formula Ingredient | g/tablet | (% w/w) |
|---|---|---|
| Phase A | | |
| Methocel A4M | 0.5000 | 59.24 |
| Avicel PH 101 ® | 0.0370 | 4.38 |
| Sodium lauryl sulfate | 0.0015 | 0.18 |
| Povidone 29K/32 | 0.0370 | 4.38 |
| Explotab ® | 0.0300 | 3.56 |
| Dye/colouring agent | 0.0040 | 0.47 |
| DI water | q.s. | q.s. |
| Phase B | | |
| Phase A | 0.6095 | 72.21 |
| Sodium lauryl sulfate | 0.0015 | 0.18 |
| Sodium starch glycolate | 0.0220 | 2.61 |
| Avicel PH 102 ® | 0.2035 | 24.11 |
| Magnesium stearate | 0.0075 | 0.89 |
| TOTAL | 0.8440 | 100.00 |

EXAMPLE 4

A formation containing Avicel PH101® intragranularly, extragranular Avicel PH 102® and Explotab® intra and extragranularly as shown in TABLE IV below exhibited an average disintegration time of less than 2 minutes in 0.1N HCl at 37$^{\pm 0.5°}$ C. using the automated disintegration apparatus.

TABLE IV

Swallowable Methylcellulose Tablets

| Formula Ingredient | g/tablet | (% w/w) |
|---|---|---|
| Phase A | | |
| Methocel A4M | 0.5000 | 59.52 |
| Avicel PH 101 ® | 0.0370 | 4.41 |
| Sodium lauryl sulfate | 0.0015 | 0.18 |
| Povidone 29K/32 | 0.0370 | 4.41 |
| Explotab ® | 0.0300 | 3.57 |
| DI water | q.s. | q.s. |
| Phase B | | |
| Phase A | 0.6055 | 72.08 |
| Sodium lauryl sulfate | 0.0015 | 0.18 |
| Sodium starch glycolate | 0.0220 | 2.62 |
| Avicel PH 102 ® | 0.2035 | 24.23 |
| Magnesium stearate | 0.0075 | 0.89 |
| TOTAL | 0.8400 | 100.00 |

In an alternative embodiment of Example 4 above, a coated version of the formulation shown in TABLE IV was tested for disintegration time. The coating solution used was 20% w/w Opadry II, Orange in water. The average disintegration time of coated tablets was less than one minute in 0.1N HCl at 37$^{\pm 0.5°}$ C. using the automated disintegration apparatus.

EXAMPLE 5

A formulation containing Avicel PH101® intragranularly, extragranular Avicel PH 102® and Explotab® intra and extragranularly as shown in TABLE V exhibited an average disintegration time of less than one minute in 0.1N HCl at 37$^{\pm 0.5°}$ C. using the automated disintegration apparatus.

TABLE V

Swallowable Methylcellulose Tablets

| Formula Ingredient | g/tablet | (% w/w) |
|---|---|---|
| *Phase A* | | |
| Methocel A4M | 0.5000 | 60.24 |
| Avicel PH 101 ® | 0.0370 | 4.46 |
| Sodium lauryl sulfate | 0.0015 | 0.18 |
| Povidone 29K/32 | 0.0370 | 4.46 |
| Explotab ® | 0.0300 | 3.62 |
| DI water | q.s. | q.s. |
| *Phase B* | | |
| Phase A | 0.6055 | 72.95 |
| Sodium lauryl sulfate | 0.0015 | 0.18 |
| Sodium starch glycolate | 0.0110 | 1.33 |
| Avicel PH 102 ® | 0.2045 | 24.64 |
| Magnesium stearate | 0.0075 | 0.90 |
| TOTAL | 0.8300 | 100.00 |

EXAMPLE 6

A formulation containing Avicel PH101® intragranularly, extragranular Avicel PH 102® and no Explotab® as shown in TABLE VI below, exhibited an average disintegration time of less than 3 minutes in 0.1N HCl and less than 2 minutes $37 \pm 0.5°$ C. using the automated disintegration apparatus. The disintegration times using the conventional apparatus were about 1 minute in acid and less than 2 minutes in water.

TABLE VI

Swallowable Methylcellulose Tablets

| Formula Ingredient | g/tablet | (% w/w) |
|---|---|---|
| *Phase A* | | |
| Methocel A4M | 0.5000 | 67.94 |
| Avicel PH 101 ® | 0.0370 | 5.03 |
| Sodium lauryl sulfate | 0.0015 | 0.20 |
| Povidone 29K/32 | 0.0370 | 5.03 |
| Dye/Colouring Agent | 0.0010 | 0.14 |
| DI water | q.s. | q.s. |
| *Phase B* | | |
| Phase A | 0.5765 | 78.34 |
| Sodium lauryl sulfate | 0.0011 | 0.15 |
| Avicel PH 102 ® | 0.1527 | 20.75 |
| Magnesium stearate | 0.0056 | 0.76 |
| TOTAL | 0.7359 | 100.00 |

EXAMPLE 7

A formulation containing corn starch intragranularly, extragranular Starch 1500 and no Explotab® as shown in TABLE VII exhibited an average disintegration time of less than 16 minutes in 0.1N HCl at $37 \pm 0.5°$ C. using the automated disintegration apparatus.

TABLE VII

Swallowable Methylcellulose Tablets

| Formula Ingredient | g/tablet | (% w/w) |
|---|---|---|
| *Phase A* | | |
| Methocel A4M | 0.5000 | 63.29 |
| Corn starch | 0.0370 | 4.68 |
| Sodium lauryl sulfate | 0.0015 | 0.19 |
| Povidone 29K/32 | 0.0370 | 4.68 |
| Dye/Colouring Agent | 0.0010 | 0.13 |
| DI water | q.s. | q.s. |
| *Phase B* | | |
| Phase A | 0.5765 | 72.97 |
| Sodium lauryl sulfate | 0.0015 | 0.19 |
| Starch 1500 ® | 0.2045 | 25.89 |
| Magnesium stearate | 0.0075 | 0.95 |
| TOTAL | 0.7900 | 100.00 |

EXAMPLE 8

A formulation containing corn starch intragranularly, extragranular Starch 1500 and intragranular Explotab® as shown in TABLE VIII exhibited an average disintegration time of less than 14 minutes in 0.1N HCl at $37 \pm 0.5°$ C. using the automated disintegration apparatus.

TABLE VIII

Swallowable Methylcellulose Tablets

| Formula Ingredient | g/tablet | (% w/w) |
|---|---|---|
| *Phase A* | | |
| Methocel A4M | 0.5000 | 61.00 |
| Corn starch | 0.0370 | 4.51 |
| Sodium lauryl sulfate | 0.0015 | 0.18 |
| Povidone 29K/32 | 0.0370 | 4.51 |
| Explotab ® | 0.0300 | 3.66 |
| Dye/Colouring Agent | 0.0010 | 0.12 |
| DI water | q.s. | q.s. |
| *Phase B* | | |
| Phase A | 0.6065 | 73.98 |
| Sodium lauryl sulfate | 0.0015 | 0.18 |
| Starch 1500 ® | 0.2045 | 24.93 |
| Magnesium stearate | 0.0075 | 0.91 |
| TOTAL | 0.8200 | 100.00 |

EXAMPLE 9

A formulation containing corn starch intragranularly, extragranular Starch 1500 and intra as well as extragranular Explotab® as shown in TABLE IX exhibited an average disintegration time of less than 13 minutes in 0.1N HCl at $37 \pm 0.5°$ C. using the automated disintegration apparatus.

TABLE IX

Swallowable Methylcellulose Tablets

| Formula Ingredient | g/tablet | (% w/w) |
|---|---|---|
| Phase A | | |
| Methocel A4M | 0.5000 | 59.88 |
| Corn starch | 0.0370 | 4.43 |
| Sodium lauryl sulfate | 0.0015 | 0.18 |
| Povidone 29K/32 | 0.0370 | 4.43 |
| Explotab ® | 0.0300 | 3.59 |
| Dye/Colouring Agent | 0.0010 | 0.12 |
| DI water | q.s. | q.s. |
| Phase B | | |
| Phase A | 0.6065 | 72.63 |
| Sodium lauryl sulfate | 0.0015 | 0.18 |
| Starch 1500 ® | 0.2045 | 24.49 |
| Explotab ® | 0.0150 | 1.80 |
| Magnesium stearate | 0.0075 | 0.90 |
| TOTAL | 0.8350 | 100.00 |

EXAMPLE 10

A formulation containing corn starch intragranularly, extragranular Starch 1500 and intra as well as extragranular Explotab® (in higher amounts than shown above in Example 9, TABLE IX) as shown in TABLE X exhibited an average disintegration time of less than 11 minutes in 0.1N HCl and less than 18 minutes in water at $37^{\pm}0.5°$ C. using the automated disintegration apparatus.

TABLE X

Swallowable Methylcellulose Tablets

| Formula Ingredient | g/tablet | (% w/w) |
|---|---|---|
| Phase A | | |
| Methocel A4M | 0.5000 | 58.82 |
| Corn starch | 0.0370 | 4.35 |
| Sodium lauryl sulfate | 0.0015 | 0.18 |
| Povidone 29K/32 | 0.0370 | 4.35 |
| Explotab ® | 0.0300 | 3.53 |
| Dye/Colouring Agent | 0.0010 | 0.12 |
| DI water | q.s. | q.s. |
| Phase B | | |
| Phase A | 0.6065 | 71.35 |
| Sodium lauryl sulfate | 0.0015 | 0.18 |
| Starch 1500 ® | 0.2045 | 24.05 |
| Explotab ® | 0.0300 | 3.54 |
| Magnesium stearate | 0.0075 | 0.88 |
| TOTAL | 0.8500 | 100.00 |

EXAMPLE 11

Various formulation containing Avicel PH101® intragranularly and different levels of extragranular Avicel PH102® (as shown in Examples 11, 12, and 13 below) were made to observe their effect on disintegration time of the tablets.

The formulation in TABLE XI, below, exhibited an average disintegration time of less than one minute in 0.1N HCl and less than 2 minutes in water at $37^{\pm}0.5°$ C. using the automated disintegration apparatus. The conventional disintegration apparatus yielded less than 1 minute in both acid and water.

TABLE XI

Swallowable Methylcellulose Tablets

| Formula Ingredient | g/tablet | (% w/w) |
|---|---|---|
| Phase A | | |
| Methocel A4M | 0.5000 | 62.42 |
| Avicel PH 101 ® | 0.0370 | 4.62 |
| Sodium lauryl sulfate | 0.0015 | 0.19 |
| Povidone 29K/32 | 0.0480 | 5.99 |
| Dye/Colouring Agent | 0.0010 | 0.12 |
| DI water | q.s. | q.s. |
| Phase B | | |
| Phase A | 0.5875 | 73.34 |
| Sodium lauryl sulfate | 0.0015 | 0.19 |
| Avicel PH 102 ® | 0.2045 | 25.53 |
| Magnesium stearate | 0.0075 | 0.94 |
| TOTAL | 0.8010 | 100.00 |

EXAMPLE 12

The formulation in TABLE XII exhibited an average disintegration time of less than 5 minutes in 0.1N HCl and less than 7 minutes in water at $37^{\pm}0.5°$ C. using the automated disintegration apparatus. The conventional disintegration apparatus yielded less than 5 minutes in acid and less than 8 minutes in water.

TABLE XII

Swallowable Methylcellulose Tablets

| Formula Ingredient | g/tablet | (% w/w) |
|---|---|---|
| Phase A | | |
| Methocel A4M | 0.5000 | 69.35 |
| Avicel PH 101 ® | 0.0370 | 5.13 |
| Sodium lauryl sulfate | 0.0015 | 0.21 |
| Povidone 29K/32 | 0.0480 | 6.66 |
| Dye/Colouring Agent | 0.0010 | 0.14 |
| DI water | q.s. | q.s. |
| Phase B | | |
| Phase A | 0.5875 | 81.48 |
| Sodium lauryl sulfate | 0.0015 | 0.21 |
| Avicel PH 102 ® | 0.1245 | 17.27 |
| Magnesium stearate | 0.0075 | 1.04 |
| TOTAL | 0.7210 | 100.00 |

EXAMPLE 13

The formulation in TABLE XIII exhibited an average disintegration time of less than 10 minutes in 0.1N HCl and less than 14 minutes in water at $37^{\pm}0.5°$ C. using the automated disintegration apparatus. The conventional disintegration apparatus yielded less than 14 minutes in acid and less than 22 minutes in water.

TABLE XIII

Swallowable Methylcellulose Tablets

| Formula Ingredient | g/tablet | (% w/w) |
|---|---|---|
| Phase A | | |
| Methocel A4M | 0.5000 | 76.10 |
| Avicel PH 101 ® | 0.0370 | 5.63 |
| Sodium lauryl sulfate | 0.0015 | 0.23 |
| Povidone 29K/32 | 0.0480 | 7.31 |
| Dye/coloring agent | 0.0010 | 0.15 |
| DI water | q.s. | q.s. |
| Phase B | | |
| Phase A | 0.5875 | 89.42 |
| Sodium lauryl sulfate | 0.0015 | 0.23 |
| Avicel PH 102 ® | 0.0605 | 9.21 |
| Magnesium stearate | 0.0075 | 1.14 |
| TOTAL | 0.6570 | 100.00 |

EXAMPLE 14

The formulation in TABLE XIV exhibited an average disintegration time of less than 7 minutes in 0.1N HCl and less than 9 minutes in water at 37±0.5° C. using the automated disintegration apparatus. The conventional disintegration apparatus yielded less than 8 minutes in acid and less than 13 minutes in water.

TABLE XIV

Swallowable Methylcellulose Tablets

| Formula Ingredient | g/tablet | (% w/w) |
|---|---|---|
| Phase A | | |
| Methocel A4M | 0.5000 | 62.42 |
| Avicel PH 101 ® | 0.0370 | 4.62 |
| Sodium lauryl sulfate | 0.0015 | 0.19 |
| Povidone 29K/32 | 0.0480 | 5.99 |
| Dye/Coloring Agent | 0.0010 | 0.12 |
| DI water | q.s. | q.s. |
| Phase B | | |
| Phase A | 0.5875 | 73.34 |
| Sodium lauryl sulfate | 0.0015 | 0.19 |
| Avicel PH200 ® | 0.2045 | 25.53 |
| Magnesium stearate | 0.0075 | 0.94 |
| TOTAL | 0.8010 | 100.00 |

All publications, including but not limited to patents and patent applications cited in this specification are herein incorporated by reference as if each individual publication were specifically and individually indicated to be incoporated by reference herein as though fully set forth.

The above description fully disloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A process for preparing a tablet formulation which process comprises:
   a) blending together to form an intragranular mixture high viscosity methylcellulose of >3000 cps; a diluent selected from the group consisting of microcrystalline cellulose, corn starch, pregelatinized starch, and mixtures thereof; and optionally a disintegrant; and
   b) adding to the mixture of step (a), a PVP aqueous solution, or alternatively spraying the mixture of step (a) with a PVP aqueous solution; and preparing granulates; and
   c) blending together an extragranular mixture of a wetting agent; a lubricating agent; and optionally a disintegrant, or a mixture thereof; and
   d) compacting the granulates of step (b) with the extragranular mixture of step (c).

2. The process according to claim 1 wherein the extragranular mixture comprises microcrystalline cellulose, sodium lauryl sulfate, and magnesium sterate.

3. The process according to claim 1 wherein the extragranular mixture comprises starch, sodium lauryl sulfate, sodium starch glycolate, and magensium sterate.

4. A process for the manufacture of a pharmaceutical tablet, which process comprises mixing
   a) granulates comprising high viscosity methylcellulose of >3000 cps; a diluent selected from the group consisting of microcrystalline cellulose, corn starch, pregelatinized starch, and mixtures thereof; and optionally an intra-granular disintegrant, and/or a wetting agent; and
   b) an extra-granular disintegrant, and a wetting agent, and optionally an extra-granular lubricant; and
   c) compressing into a tablet.

5. The process according to claim 1 wherein the extragranular mixture further comprises sodium starch glycolate.

6. The process according to claim 5 wherein the sodium starch glycolate is present in an amount of about 3 to about 7% w/w.

7. The process according to claim 1 wherein the diluent of step (a) is microcrystalline cellulose.

8. The process according to claim 1 wherein the diluent of step (a) is microcrystalline cellulose and is present in a ratio of methylcellulose to microcrystalline cellulose from about 2.1 to about 14:1.

9. The process according to claim 1 wherein the diluent of step (a) is corn starch and is present in a ratio of methylcellulose to cornstarch of from about 7.5 to about 15:1.

10. The process according to claim 1 wherein the diluent of step (a) is pregelatinized starch and is present in a ratio of methylcellulose to starch of from about 2.0 to about 5.0:1.

* * * * *